(12) United States Patent
Kasen et al.

(10) Patent No.: US 6,840,093 B2
(45) Date of Patent: Jan. 11, 2005

(54) SYSTEM AND METHOD FOR DETERMINING OIL GRADE

(75) Inventors: Jon E. Kasen, E. Peoria, IL (US); Michelle A. Lee, Edelstein, IL (US)

(73) Assignee: Caterpillar Inc., Peoria, IL (US)

(*) Notice: Subject to any disclaimer, the term of this patent is extended or adjusted under 35 U.S.C. 154(b) by 343 days.

(21) Appl. No.: 10/117,622

(22) Filed: Apr. 5, 2002

(65) Prior Publication Data

US 2003/0188570 A1 Oct. 9, 2003

(51) Int. Cl.[7] .............................................. G01N 33/18
(52) U.S. Cl. ............................. 73/61.78; 73/54.02
(58) Field of Search ........................... 73/53.01, 54.02, 73/61.76, 61.78

(56) References Cited

U.S. PATENT DOCUMENTS

| | | |
|---|---|---|
| 4,675,662 A | 6/1987 | Kondo et al. |
| 4,785,287 A | 11/1988 | Honma et al. |
| 5,750,887 A | 5/1998 | Schricker |
| 5,789,665 A | 8/1998 | Voelker et al. |
| 5,986,546 A | 11/1999 | Kramer |
| 5,987,976 A | 11/1999 | Sarangapani |
| 6,050,130 A | 4/2000 | Kramer |
| 6,152,107 A * | 11/2000 | Barnes et al. ............... 123/357 |
| 6,216,528 B1 | 4/2001 | Carrell et al. |
| 6,223,589 B1 | 5/2001 | Dickert et al. |
| 6,415,652 B1 | 7/2002 | Carrell et al. |
| 2002/0083758 A1 * | 7/2002 | Carrell et al. .............. 73/54.02 |

* cited by examiner

Primary Examiner—Hezron Williams
Assistant Examiner—John Fitzgerald
(74) Attorney, Agent, or Firm—Michael R Huber; Steven D Lundquist

(57) ABSTRACT

The grade of oil used in a machine or apparatus can be determined by determining a temperature and pressure within an oil supply and determining the oil grade in response to determining the temperature and pressure.

18 Claims, 1 Drawing Sheet

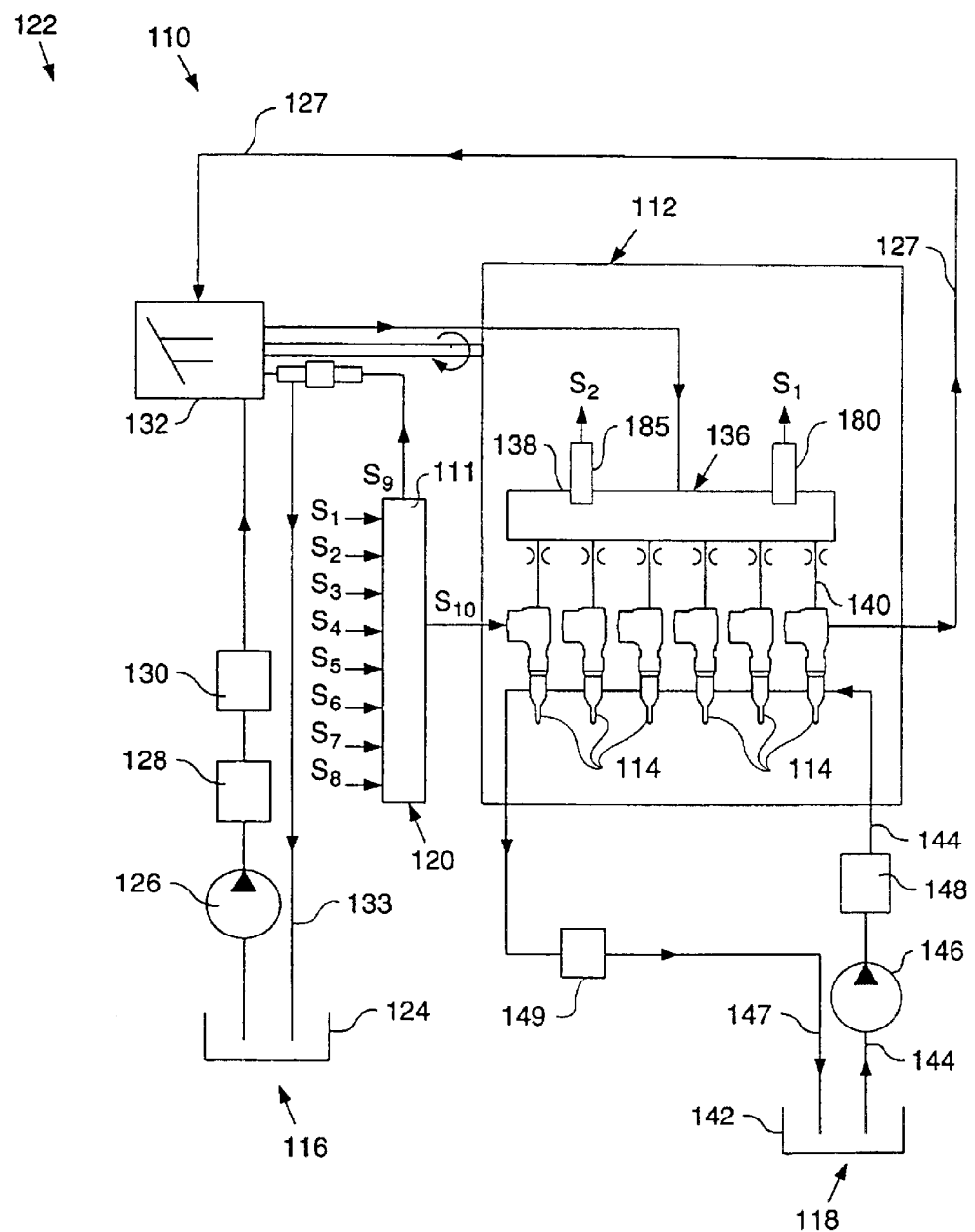

US 6,840,093 B2

SYSTEM AND METHOD FOR DETERMINING OIL GRADE

TECHNICAL FIELD

The present invention relates to determining the grade of oil used in a machine or apparatus.

BACKGROUND

Oil is used in numerous applications and is commonly used as a lubricant in engines. Due to the broad range of engines and operating environments, lubrication oil is available in a variety of different viscosities (formulations, weights, or grades). For example, lubrication oil could be a single viscosity oil, such as SAE 30 base oil, which has a viscosity of 30 at a set testing temperature or lubrication oil could be a multi-viscosity oil, such as 15W40, 0W30, or 10W30. With multi-viscosity oils, the first number indicates a first viscosity at a first temperature (a cold temp.) and the second number indicates the oil's second viscosity at a second temperature (a hot temp.) Multi-viscosity oils are beneficial in engine use to help handle the diverse operating environments, such as cold start.

In some devices or engine systems, lubrication oil is also used as an actuation fluid for hydraulically actuated devices. For example, because lubrication oil is a common fluid source in engine systems, it is relatively easy to employ for hydraulic "muscle" in hydraulically actuated electronically controlled unit injectors or hydraulically actuated or partially actuated valves. By using hydraulic power, actuation events can be controlled independently of the engine speed (eliminating dependency on the cam shaft) and enhance engine performance. Specifically, in unit injectors, oil is pressurized to relatively high levels and is used in conjunction with an intensifier piston to pressurize fuel to injection pressure. With valves, the pressurized oil can be used to open intake or exhaust valves.

Although lubrication oil is a preferred actuation fluid in engine systems, it does have some drawbacks. The viscosity of the oil can impact the timing of the desired actuation event which, in turn, impacts engine performance. This is most common during cold starting. Often, look up tables for each grade of oil are used within the engine's electronic control unit (ECU) to help predict and adjust for an oil's viscosity at a specific temperature. Unfortunately, the oil grade used in the engine is often not known, so choosing which look up table to use is difficult and can result in decreased engine performance. Although engine manufactures may specify a specific lubrication oil to use, many customers and service providers may use different oil varieties, requiring manufactures to design engines to account for different oil types.

The present invention is intended to address one or more of the above problems.

SUMMARY OF THE INVENTION

In a first embodiment of the present invention, a method of oil grade detection comprises measuring a temperature in an oil supply, measuring a pressure in the oil supply, and determining the oil grade in response to measuring the temperature and pressure.

In a second embodiment, a system for determining oil grade comprises a temperature sensor, a pressure sensor, and an electronic control module connected to the temperature sensor and pressure sensor, wherein the electronic control module receives a temperature signal and a pressure signal from the sensors and determines the oil grade in response to the temperature and pressure signal.

In a third embodiment, a method of oil grade detection comprises measuring a temperature of an oil supply; measuring a pressure of the oil supply; measuring a duration of an event drawing oil from the oil supply; measuring a second pressure of the oil supply; estimating a pressure drop of a variety of oil grades in response to the temperature and duration; determining an actual pressure drop of the oil supply in response to measuring the first and second pressures; comparing the actual pressure drop to the estimated pressure drop; and determining the oil grade in response to the comparing step.

In a fourth embodiment of the present invention, a method of determining oil grade comprises determining a pressure drop in an oil supply, determining a temperature in the oil supply, an determining the oil grade in response to the pressure drop and temperature.

BRIEF DESCRIPTION OF THE DRAWINGS

FIG. 1 is a schematic illustration of a fuel system according to one embodiment of the present invention.

DETAILED DESCRIPTION

FIG. 1 illustrates an embodiment of a hydraulically actuated electronically controlled fuel injection system 110 in an example configuration as adapted for a direct-injection diesel-cycle internal combustion engine 112. Fuel system 110 includes one or more hydraulically-actuated electronically-controlled fuel injectors 114, positioned in a respective cylinder head bore (not shown) of engine 112. Fuel system 110 includes a first source of pressurized fluid flow 116 for supply of actuating fluid to each injector 114, a second source of pressurized fluid flow 118 for supplying fuel to each injector, a computer 120 for electronically controlling the fuel injection system and an apparatus 122 for re-circulating actuation fluid leaving each of the injectors.

The first fluid source 116 preferably includes an actuating fluid sump 124, a relatively low pressure actuating fluid transfer pump 126, an actuating fluid cooler 128, one or more actuation fluid filters 130, a high pressure pump 132 for generating relatively high pressure in the actuation fluid and at least one relatively high pressure actuation fluid manifold 136. A oil rail passage 138 is arranged in fluid communication with the outlet from the relatively high pressure actuation fluid pump 132. A rail branch passage 140 connects the actuation fluid inlet of each injector 114 to the high pressure oil rail passage 138.

Actuation fluid leaving an actuation fluid drain of each injector 114 enters a re-circulation line 127 that carries the same to the actuation fluid re-circulating apparatus 122. A portion of the re-circulated actuation fluid is channeled to high pressure actuation fluid pump 132 and another portion is returned to actuation fluid sump 124 via re-circulation line 133.

In a preferred embodiment, the actuation fluid is engine lubricating oil and the actuation fluid sump 124 is an engine lubrication oil sump. This allows the fuel injection system to be connected as a parasitic subsystem to the engine's lubricating oil circulation system.

The second fluid source 118 preferably includes a fuel tank 142, a fuel supply passage 144 arranged in fluid communication between fuel tank 142 and the fuel inlet of each injector 114, a relatively low pressure fuel transfer pump 146, one or more fuel filters 148, a fuel supply regulating valve 149, and a fuel circulation and return passage 147 arranged in fluid communication between injectors 114 and fuel tank 142.

The computer 120 preferably includes an electronic control module (ECM) 111 including a microprocessor and memory. As is known to those skilled in the art, the memory is connected to the microprocessor and stores an instruction sets, variables and maps (or look-up tables) which provide information or instructions based upon certain known conditions. Associated with the microprocessor and part of the ECM 111 are various other known circuits such as power supply circuitry, signal conditioning circuitry and solenoid driver circuitry, among others. The ECM 111 controls a variety of engine functions and injection parameters including: 1) the fuel injection timing; 2) the total fuel injection quantity during an injection cycle; 3) the fuel injection pressure; 4) the number of separate injections or injection segments during each injection cycle; 5) the time intervals between the injection segments; 6) the fuel quantity of each injection segment during an injection cycle; 7) the actuation fluid pressure; 8) current level of the injector waveform; and 9) any combination of the above parameters. ECM 111 receives a plurality of sensor input signals S1–S8, which correspond to known sensor inputs, such as engine operating conditions including engine speed, engine temperature, pressure of the actuation fluid, temperature of the actuation fluid, load on the engine, etc., as well as desired operating conditions such as desired engine speed, that are used to determine the precise combination of injection parameters for a subsequent injection cycle.

For example, a rail temperature sensor 180 is connected to an oil rail passage 138 and produces a signal, designated S1, responsive to the temperature of the actuating fluid. The signal S1 is input into the ECM 111. Another example of an engine sensor input is a rail pressure sensor 185 shown connected to the high pressure oil rail passage 138 for producing a high pressure signal S2 responsive to the pressure of the actuating fluid. Commonly, the signals S1 and S2 are voltages created by the sensor where the voltage created depends upon the measured condition.

In this example, ECM 111 issues control signal S9 to control the actuation fluid pressure and a fuel injection signal S10 to energize a solenoid within a fuel injector thereby controlling fluid control valve(s) within each injector 114 and causing fuel to be injected into a corresponding engine cylinder. Each of the injection parameters are variably controllable, independent of engine speed and load. In the case of injector 114, control signal S10 is a fuel injection signal that is a computer commanded current to the injector solenoid. In controlling injector 114, ECM 111 can control injector 114 in a variety of ways using signal S10 including using multiple signals, such as sending a signal to turn on, a second signal to maintain, and a third signal to turn off, or ECM 111 could simply use one signal wherein when the signal is sent to injector 114, it is on, and when the signal is terminated, injector 114 turns off.

Fuel injectors 114 are capable of multiple injections or injection segments per engine cycle. As stated previously, the ECM 111 controls when, duration and number of injections or segments for each injector 114 per engine cycle. Multiple injections or injection segments are well know in the art and may include pilots, mains, posts, and anchors.

In order to obtain desired engine performance and emissions, it is necessary to understand how injector 114 is operating and adjust or trim the injector's 114 operation accordingly. Trimming an injector often includes adjusting the timing of signal S10 from the ECM to account for variables in the injector or fuel system. For example, if injector 114 was injecting fuel earlier than desired, the timing of signal S10 could be delayed so that the injection timing could occur when desired.

One parameter that influences injector operation and performance is the viscosity of the oil. The viscosity of the oil can significantly impact the timing of the injection event, especially during cold start, when the oil is more viscous and responds slower. Slower moving oil effects the injection rate, quantity and time. In order to accommodate for the viscosity of the oil, injection parameters including the timing, quantity and rate, must be adjusted; but in order to trim the injection event, it is necessary to know the viscosity of the oil. Unfortunately, determining the viscosity of the oil with a viscosity sensor is not necessarily practical in an engine system, however, because the viscosity of the oil is a function of the oil grade, if the oil grade is known, along with the temperature of the oil, the viscosity can be sufficiently estimated.

In the system illustrated in FIG. 1, ECM 111 sends an actuation signal S10 to injector 114 when an injection is desired. This causes injector 114 to draw oil from the oil rail passage 138 to pressurize fuel for injection into the combustion chamber (not shown). Concurrently with sending the actuation signal S10, rail temperature sensor 180 measures the temperature of the oil in oil rail passage 138 and sends a signal S1 to the ECM 111. Additionally, rail pressure sensor 185 determines the oil pressure in the rail at the beginning of the injection event and sends a signal S2 to ECM 111. When the injection event is finished, ECM 111 terminates injection signal S10 and determines how long the injection event lasted. At this point, a second pressure reading is made by rail pressure sensor 185 and a signal S2 is sent ECM 111. It is preferred that the oil temperature and pressure are determined in close proximity to the oil draining event in order to obtain the most accurate data possible; however it may be necessary to adjust the timing of the measurements in order to account for other events that may be occurring in the system.

From the data captured through the injection event, ECM 111 can determine which oil grade is present in the system 110. First, because ECM 111 knows the duration of the injection event (the time ECM 111 started sending signal S10 to injector 114 until the time signal S10 was terminated), it can estimate how much oil should have been drawn into injector 114 at the specific temperature measured by rail temperature sensor 180. From this an estimated rail pressure drop can be determined. (The rail pressure drop is a result of oil being "pulled out" of the oil rail passage 138 into injector 114 to actuate an intensifier piston (not shown) to pressurize the fuel). However, as stated previously, each type of oil could have a different viscosity, which would impact what the actual rail pressure drop was; therefore, rail pressure drops are estimated for a variety of oil types. Preferably, rail pressure drops would be estimated for all oil types that may be used with in the engine, such as 15W40, 0W30 and 10W30.

ECM 111 can also determine what the actual rail pressure drop was. A first rail pressure was measured by rail pressure sensor 180 at the beginning of the injection event and a second rail pressure was measured at the end of the injection event. From these two measurements, ECM 111 can determine the actual pressure drop for oil rail passage 138. ECM 111 compares the actual pressure drop to the estimated pressure drops for each type of oil. ECM 111 determines which estimated pressure drop matches the actual pressure drop, and from that determines which oil grade is present in system 110. Once the grade of oil is known, ECM 111 can then choose an appropriate viscosity/temperature map for the specific oil grade to properly adjust/trim injection parameters, including rate, quantity, and timing.

INDUSTRIAL APPLICABILITY

Determining the grade of oil in a machine, vehicle or system allows control of the system to be altered/trimmed in response to the oil grade. This can be especially important when the operating environment varies significantly which results in a wide range of physical properties, such as viscosity, for the oil depending on the conditions. As the properties of the oil change, the performance of the system can be adversely affected.

Oil grade detection can be implemented in a variety of systems. As illustrated above, it can be used in a system using hydraulically actuated electronically controlled unit injectors, but oil grade detection can also be used for other hydraulically actuated engine systems, such as controlling engine intake and exhaust valves. Oil grade detection could also be used in automobiles for determining the grade of oil present in a car's lubrication system.

The above illustration also showed the system using sensors that directly measured rail pressure and temperature; however, other indirect sensing methods could be used. For example, oil temperature could be measured in the sump, pump, or injector. Further, the temperature could be indirectly determined, estimated or inferred by measuring the temperature or properties of other engine components or systems, such as the coolant or engine block. Similar indirect methods could be used to measure, determine or estimate the oil rail pressure, such as monitoring high pressure pump activity or injector activity to determine the pressure drop of the oil rail.

Other aspects, features, and advantages of the present invention may be obtained from a study of this disclosure and the drawings, along with the appended claims.

What is claimed is:

1. A method for determining an oil grade comprising:
   determining a temperature in an oil supply;
   determining a first pressure in said oil supply;
   determining a second pressure in said oil supply;
   determining an actual pressure drop from said first and second determined pressures;
   determining a plurality of estimated pressure drops for each of a plurality of oil grades at said temperature;
   comparing said actual pressure drop to each of said plurality of estimated pressure drops; and
   determining said oil grade in response to said actual pressure drop matching one of said estimated pressure drop.

2. The method of claim 1 wherein determining an estimated pressure drop includes:
   determining a duration of an event drawing oil from said oil supply; and
   estimating said pressure drop for said variety of oil types in response to said determining temperature step and said determining duration step.

3. The method of claim 1 further including:
   adjusting an injector timing in response to said oil trade determining step.

4. The method of claim 1 further including:
   adjusting a valve timing in response to said oil grade determining step.

5. The method of claim 1 further including:
   trimming a hydraulic component in response to said oil grade determining step.

6. A system for determining an oil grade comprising:
   a temperature sensor;
   a pressure sensor; and
   an electronic control module connected to said temperature sensor and said pressure sensor; wherein said electronic control module receives a temperature signal from said temperature sensor and determines a plurality of estimated pressure drops for each of a plurality of oil grades at said temperature, and wherein said electronic control module further receives first and second pressure signals from said pressure sensor, determines an actual pressure drop from said first and second pressure signals, compares said actual pressure drop to each of said plurality of estimated pressure drops and determines said oil grade in response to said actual pressure drop matching one of said estimated pressure drops.

7. The system of claim 6 wherein said temperature sensor is located in an oil supply rail.

8. The system of claim 6 wherein said pressure sensor is located in an oil supply rail.

9. The system of claim 6 wherein said temperature sensor is an oil temperature sensor.

10. The system of claim 6 wherein said electronic control module trims a hydraulic component in response to said determining said oil grade.

11. The system of claim 10 wherein said hydraulic component is a fuel injector.

12. The system of claim 10 wherein said hydraulic component is a valve.

13. A method of determining an oil grade of an oil supply comprising:
    measuring a temperature of said oil supply;
    measuring a first pressure of said oil supply;
    measuring a duration of an event drawing oil from said oil supply;
    measuring a second pressure of said oil supply;
    estimating a pressure drop for each of a variety of oil grades in response to said temperature and said duration;
    determining an actual pressure drop of said oil supply in response to measuring said first pressure and measuring said second pressure;
    comparing said actual pressure drop to each of said estimated pressure drops; and
    determining said oil grade in response to said comparing step.

14. The method of claim 13 including:
    measuring said first pressure before said event.

15. The method of claim 13 including:
    measuring said first pressure proximate in time to a start of said event.

16. The method of claim 13 including:
    measuring said second pressure at an end of said event.

17. The method of claim 13 including:
    measuring said second pressure proximate in time to an end of said event.

18. The method of claim 13 including:
    trimming a hydraulic component in response to said determining said oil grade step.

* * * * *